(12) United States Patent
Sughrue et al.

(10) Patent No.: US 11,315,676 B2
(45) Date of Patent: Apr. 26, 2022

(54) CLINICAL INFRASTRUCTURE WITH FEATURES FOR THE PREVENTION OF EGRESS OF PRIVATE INFORMATION

(71) Applicant: Omniscient Neurotechnology Pty Limited, Sydney (AU)

(72) Inventors: Michael Edward Sughrue, Sydney (AU); Stephane Philippe Doyen, Glebe (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/342,420

(22) Filed: Jun. 8, 2021

(65) Prior Publication Data

US 2021/0392118 A1     Dec. 16, 2021

Related U.S. Application Data

(60) Provisional application No. 63/038,400, filed on Jun. 12, 2020.

(51) Int. Cl.
| | |
|---|---|
| *H04L 9/32* | (2006.01) |
| *G16H 30/20* | (2018.01) |
| *G06T 7/00* | (2017.01) |
| *G06T 11/00* | (2006.01) |
| *G06F 9/455* | (2018.01) |

(Continued)

(52) U.S. Cl.
CPC .......... *G16H 30/20* (2018.01); *A61B 5/0013* (2013.01); *A61B 5/0022* (2013.01); *A61B 5/4064* (2013.01); *G06F 9/451* (2018.02); *G06F 9/45558* (2013.01); *G06T 7/0012* (2013.01); *G06T 11/00* (2013.01); *G16H 10/60* (2018.01); *G16H 30/40* (2018.01); *H04L 9/32* (2013.01); *H04L 63/0428* (2013.01); *G06T 2207/20092* (2013.01); *G06T 2207/30016* (2013.01)

(58) Field of Classification Search
CPC .................................................. H04L 630/428
USPC .................................................. 713/168
See application file for complete search history.

(56) References Cited

U.S. PATENT DOCUMENTS

| | | |
|---|---|---|
| 8,086,077 B2 | 12/2011 | Eichhorn et al. |
| 8,407,244 B2 | 3/2013 | Canessa et al. |
| | (Continued) | |

OTHER PUBLICATIONS

David B. Keator; A National Human Neuroimaging Collaboratory Enabled by the Biomedical Informatics Research Network (BIRN); IEEE: 2008; pp. 162-172.*

(Continued)

*Primary Examiner* — Monjur Rahim
(74) *Attorney, Agent, or Firm* — Fish & Richardson P.C.

(57) ABSTRACT

DICOM data is automatically prepared for transit outside of the clinical-data infrastructure, by examining a plurality of metadata fields in the corresponding metadata in the DICOM data; identifying a first subset of the metadata fields as containing private information; identifying a second subset of the metadata fields as private-information free; accessing at least some of the plurality of layers of the DICOM data; and transforming the accessed layers into a single transmission-image, the transmission-image being in a format i) other than DICOM and ii) that stores the second subset of the metadata fields as transmission-metadata in a scheme that is non-redundant for a given transmission-image.

20 Claims, 8 Drawing Sheets

(51) Int. Cl.
*A61B 5/00* (2006.01)
*G16H 10/60* (2018.01)
*G16H 30/40* (2018.01)
*G06F 9/451* (2018.01)
*H04L 29/06* (2006.01)

(56) References Cited

U.S. PATENT DOCUMENTS

| | | | |
|---|---|---|---|
| 8,553,965 B2 | 10/2013 | Hu et al. | |
| 9,424,432 B2 | 8/2016 | Holland et al. | |
| 10,331,852 B2 | 6/2019 | Axerio-Cilies et al. | |
| 10,817,622 B2 * | 10/2020 | Rosenberg | H04L 63/0428 |
| 2006/0064328 A1 | 3/2006 | Datta et al. | |
| 2007/0027715 A1 * | 2/2007 | Gropper | G16H 10/60 |
| | | | 705/2 |
| 2011/0110568 A1 | 5/2011 | Vesper et al. | |
| 2013/0094728 A1 | 4/2013 | Devries | |
| 2013/0097086 A1 | 4/2013 | Dala et al. | |
| 2013/0208955 A1 * | 8/2013 | Zhao | G16H 30/20 |
| | | | 382/128 |
| 2013/0208966 A1 * | 8/2013 | Zhao | G06F 9/5072 |
| | | | 382/131 |
| 2014/0142984 A1 | 5/2014 | Wright et al. | |
| 2016/0004820 A1 | 1/2016 | Moore | |
| 2016/0124949 A1 * | 5/2016 | Chau | G06F 16/51 |
| | | | 707/665 |
| 2016/0307063 A1 | 10/2016 | Bright et al. | |
| 2019/0243911 A1 * | 8/2019 | Kobozev | G16H 30/20 |
| 2020/0057867 A1 | 2/2020 | Aunger et al. | |
| 2020/0089911 A1 | 3/2020 | Kagiwada | |
| 2020/0143084 A1 * | 5/2020 | Rosenberg | G16H 40/20 |
| 2020/0273551 A1 * | 8/2020 | Calderon | G16H 50/20 |
| 2020/0367970 A1 * | 11/2020 | Qiu | G16H 50/50 |
| 2021/0142177 A1 * | 5/2021 | Mallya | G06N 3/04 |

OTHER PUBLICATIONS

PCT International Search Report and Written Opinion in International Appln. No. PCT/AU2021/050588, dated Aug. 16, 2021, 14 pages.

* cited by examiner

CLINICAL INFRASTRUCTURE WITH FEATURES FOR THE PREVENTION OF EGRESS OF PRIVATE INFORMATION

CROSS-REFERENCE TO RELATED APPLICATIONS

This application claims the benefit under 35 U.S.C. § 119(e) of the filing date of U.S. Patent Application No. 63/038,400, for CLINICAL INFRASTRUCTURE WITH FEATURES FOR THE PREVENTION OF EGRESS OF PRIVATE INFORMATION, which was filed on Jun. 12, 2020 and which is incorporated here by reference in its entirety.

TECHNICAL FIELD

This document describes networking technology.

BACKGROUND

A computer network is a group of computers that use a set of common communication protocols over digital interconnections for the purpose of sharing resources located on or provided by the network nodes. The interconnections between nodes are formed from a broad spectrum of telecommunication network technologies, based on physically wired, optical, and wireless radio-frequency methods that may be arranged in a variety of network topologies.

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities.

SUMMARY

Technology described in this document can be used for the prevention of egress of private information from a clinical data-infrastructure. In one implementation, computer-readable media stores instructions that, when executed by one or more processors, cause the one or more processors to perform operations. The operations include receiving DICOM data to be sent to a cloud-service provider, the DICOM data comprising a plurality of images and for each image corresponding metadata, the cloud-service provider being outside of clinical-data infrastructure. The operations include preparing, automatically, the DICOM data for transit outside of the clinical-data infrastructure, by: examining a plurality of metadata fields in the corresponding metadata in the DICOM data; identifying a first subset of the metadata fields as containing private information; identifying a second subset of the metadata fields as private-information free; accessing at least some of the plurality of layers of the DICOM data; and transforming the accessed layers into a single transmission-image, the transmission-image being in a format i) other than DICOM and ii) that stores the second subset of the metadata fields as transmission-metadata in a scheme that is non-redundant for a given transmission-image. The operations include instantiating a gap server configured to encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data; transmit to the cloud-service provider and with a unique identifier, an encrypted transmission-image made from the transmission-image and an encrypted transmission-metadata made from the transmission metadata; receive a response-message from the cloud-service including the unique identifier; and determine that the unique identifier is stored in a private-information datastore indexed with the private information, the private-information datastore also storing additional-private information indexed with other identifiers; and based on the unique identifier, provide the private information and the response-message to a client on the clinical-data infrastructure. Other implementations can include devices, software, methods, and products.

Implementations can include all, some, or none of the following features. The operations further include receiving, from the cloud-service provider, an update message with an update to the instructions; and engaging, free of intervention by administration of the clinical-data infrastructure, an update routine to the instructions. Engaging, free of intervention by administration of the clinical-data infrastructure, the update routine comprises engaging the update routine without specific user input and without specific user output. The operations further include comparing, before receiving the update message, the instructions with a latest-published version hosted by the cloud-service provider to determine if the instructions are out of date; and responsive to determining that instructions are out of date, requesting the update message. The update comprises updates to only some, but not all, of the instructions. Receiving DICOM data to be sent to the cloud-service provider comprises receiving transmission-specific user input. The transmission-specific user input is received in a graphic user interface (GUI) with user-controls to transmit the DICOM data, the GUI being free of user-controls to convert the DICOM data to the transmission-image. Transforming the accessed layers into a single transmission-image comprises maintaining, with the transmission image, transmission-metadata created from the second subset of the metadata fields, such that: the transmission-metadata is stored in computer-memory free of redundancy beyond disk-redundancy to which other data stored in the memory is subjected to; and the transmission-metadata is free of the private information of the first subset of the metadata fields in the DICOM data. The instructions comprise only sending data to the cloud service through the gap server.

Implementations can provide all, some, or none of the following advantages. The technology of computer networking, including the management of private information on a network, is improved. This technology can be used to advantageously protect private information gathered during medical imaging even when the medical images are sent outside of the clinical-data infrastructure on which it is generated. This can allow the users of the clinical-data infrastructure to access services the infrastructure cannot provide while still retaining confidence that private data never leaves the clinical-data infrastructure. This technology can be easy to use and seamless for both the users interacting with graphic user interfaces (GUI) as well as for network administrators. For example, the stripping of private information can occur without specific input to do so by users. As another example, updates to the technology can be distributed without the need of a network administrator to personally intervene in the update process.

This technology can advantageously reduce redundant data stored in computer memory and/or transmitted over computer networks. For example, redundant metadata fields can be copied one time into a new data object so that the data object stores only a single copy of the metadata. This new object can thus be stored, transmitted, and analyzed with fewer resources than the original.

DESCRIPTION OF DRAWINGS

Like reference symbols in the various drawings indicate like elements

DETAILED DESCRIPTION

Described here is technology for preparing imaging data for transmission to a cloud-service provider. For example, a clinical-data client can receive Digital Imaging and Communications in Medicine (DICOM) data from a functional imaging scan and sort out the private metadata (e.g., patient name) from non-private metadata (e.g., operational settings of imager) and pack the non-private metadata into a Neuroimaging Informatics Technology Initiative (NIfTI) file format. Further, the client may convert the many 2D image-layers of the DICOM format into a single 3D NifTI visualization.

The client may operate in a web browser or as other software that is seamless for both the user operating the client as well as administrators that administer the network. For the user, the GUI may be clutter free and provide either no or minimal interaction to convert private-data-full DICOM file format into a private-data-free NifTI imagefile format, which can advantageously reduce interactions and training required to use the client. Similarly, since the software may enable automatic updates and work in commonly deployed browsers, for example, as a webpage or plug-in, the software on the client may require little to no special administration to execute the data conversion and upload tasks described here.

Figure 1:
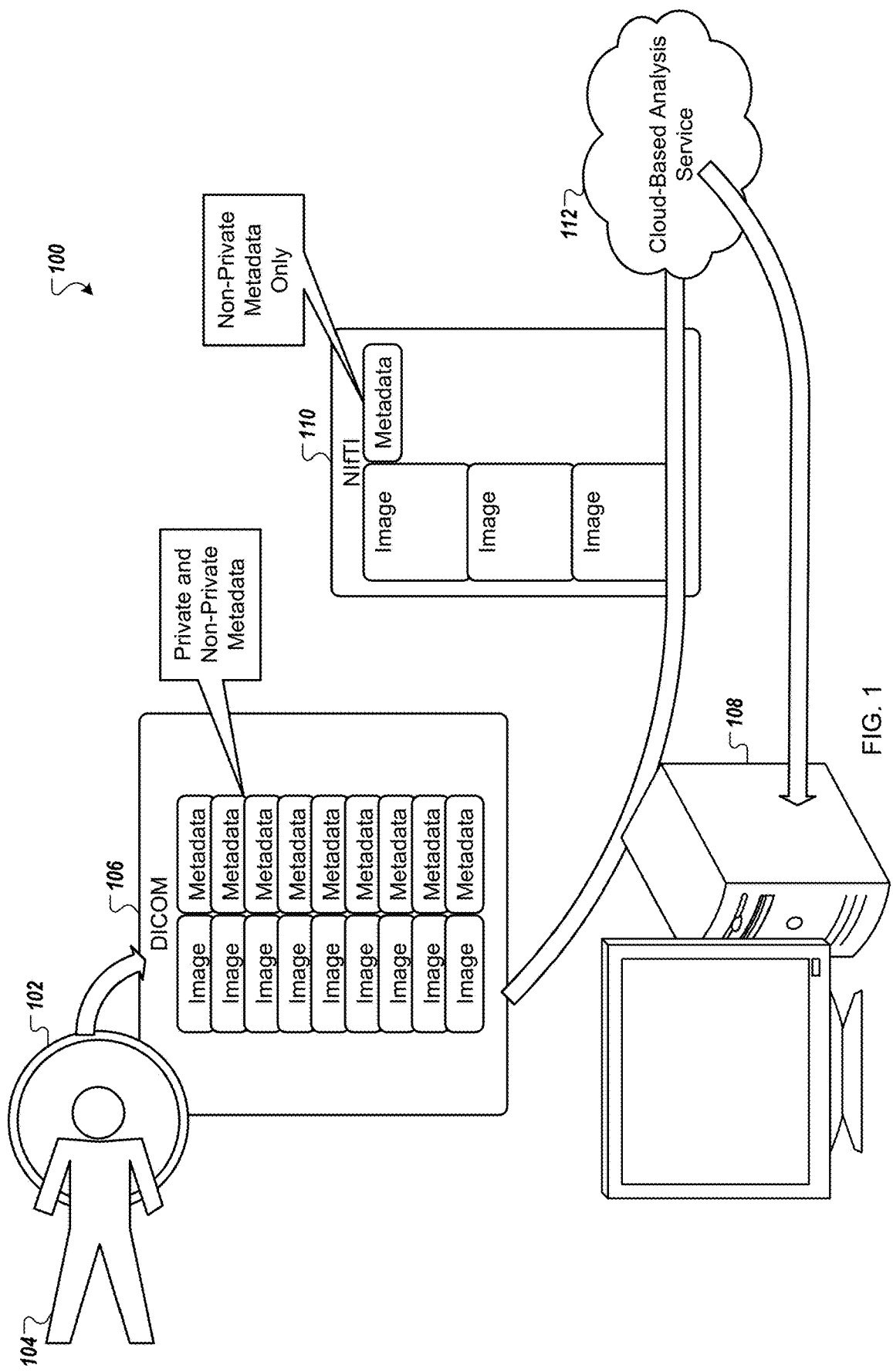
FIG. 1 shows an example system for generating medical images free of private information and also free of redundant metadata.

FIG. 1 shows an example system 100 for generating medical images free of private information and also free of redundant metadata. In the system 100, a medical imager 102 images a patient 104 to generate DICOM data 106 for a clinical-data client 108. The client 108 prepares, from the data 106, a NifTI image 110 free of private information and provides the image 110 to a cloud-bases analysis service 112, and the service 112 returns analysis to the client 108 or to another recipient machine on the same clinical-data infrastructure as the client 108.

For example, a patient's clinician may determine that the patient's treatment requires an imaging study such as a Functional Magnetic Resonance Imaging (fMRI) study. An MRI machine 102 can be used to image the patient's brain, and may produce data in its native format of DICOM, creating the data 108. The data 108 produced by the machine 102 can include a collection of 2D images taken at various time points. For each of the 2D images, the data 108 also includes a single associated metadata object with multiple fields. These metadata fields in the data 108 can include private information (e.g., patient personal information such as patient name, date of scan, birth date, sex, age, weight). In addition, the metadata fields in the data 108 can include non-private information (e.g., machine manufacturer and model, modalities in study, modality of a particular 2D image, study description, scanner parameters for a specific acquisition session).

The clinician can use the client 108 to send data from the study to the analysis service 112. In this example, the service 112 is a remotely hosted software service sometimes called a cloud service. For example, the service 112 can perform computationally intensive analysis on the data, can perform proprietary or otherwise secret analysis, etc. This can include, but is not limited to, providing data visualization, surgical planning, brain network visualization, anomaly detection in brain activity, and segregation of brain networks. In order to protect patient privacy, the client 106 can identify and remove all private information not needed for the service 112, while maintaining the non-private information that will allow the service 112 to perform its operations on behalf of the patient. In addition, to increase network, storage, and computational efficiency, the client 106 can convert the data 106 into the image 110. This may include, for example, converting stacks of 2D, pixel based, images into 3D, voxel based, images and also can include storing each item of metadata uniquely instead of redundantly, as is done in the data 110.

The service 112 can then receive this smaller, more efficient, privacy-protecting image 110 and perform one or more services based on the image 110. Results of the service then can be routed back to the client 108, or to another appropriate client (e.g., the clinician's office computer, a datastore holding the patient's electronic data records).

Figure 2:
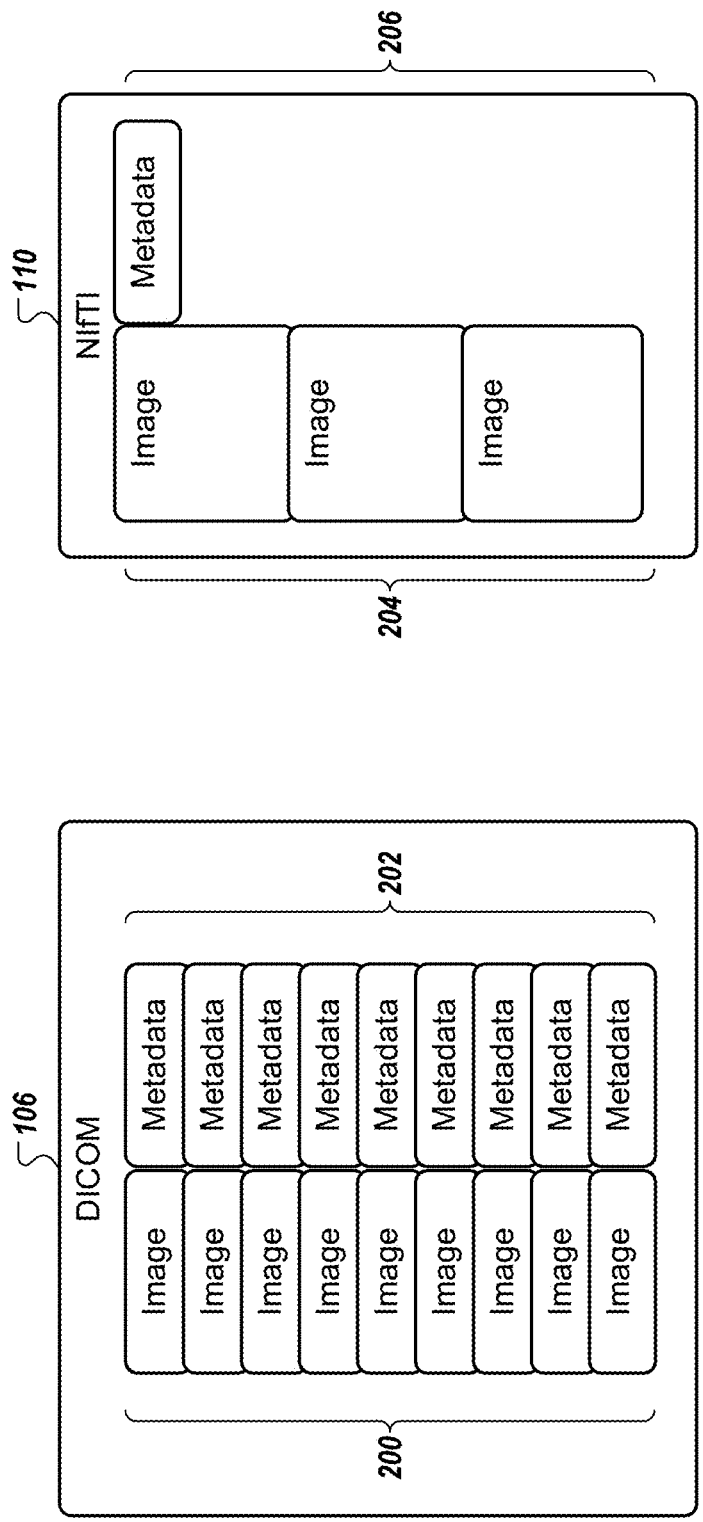
FIG. 2 shows an example of data generated by medical imaging.

FIG. 2 shows an example of data 106 generated by medical imaging and an associated image 110 made from the data 106. The data 106 and image 110 may be generated, stored in computer memory, transmitted across computer networks, etc. in binary format.

In a single study, many 2D images 200 are generated as part of the data 106. For each of the images, a corresponding metadata file 202 is created. In each of the metadata files 202, metadata related to the study is stored in metadata fields. Many of these fields contain information that does not change from image to image. The result of which is that the format of the data 106 contains many redundant values for all or many of the images 202. In addition to this logical redundancy, the data 106 may be subjected to transmission redundancy where bits of the data 106 are redundantly transmitted regardless of the contents of the data 106 (e.g., when packets are lost in transport), storage redundancy where bits of the data 106 are redundantly written to disk regardless of the contents of the data 106 (e.g., in a Redundant Array of Independent Disks (RAID) array), etc.

The image 110 is generated from the data 106. For example, the client 108 can generate the image 110 from the data 106. In the image 106, multiple 2D images 200 are combined to create 3D images 204. For example, all images 200 with the same timestamp, or that are created in one pass, can be combined, turning the stack of pixels into a field of voxels.

The metadata 206 is created from the metadata 202. However, unlike the metadata 202, the metadata 206 does not store data in logical redundancy. That is, the format of the image 110 only calls for a single instance of each metadata field. However, the image 110 may be subject to other types of redundancy. For example, the image 110 may be subjected to transmission redundancy where bits of the image 110 are redundantly transmitted regardless of the contents of the image 110 (e.g., when packets are lost in transport), storage redundancy where bits of the image 110 are redundantly written to disk regardless of the contents of the image 110 (e.g., in a Redundant Array of Independent Disks (RAID) array), etc. In one example, data 106 with a size of more than 200 Mb, e.g., 220 Mb, may be converted into a corresponding image 110 with a size of less than 10 Mb, e.g., 7 Mb.

Figure 3:
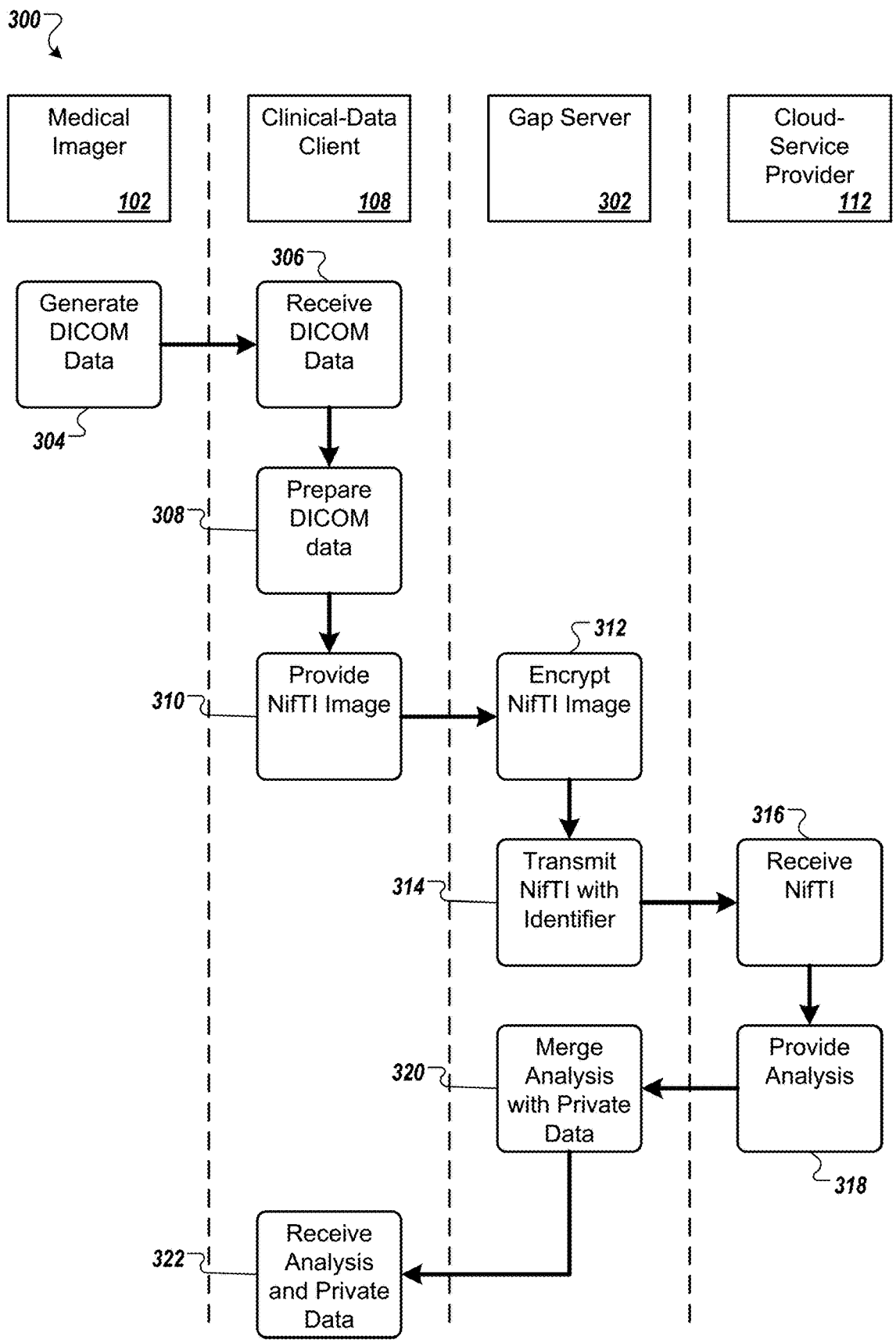
FIG. 3 shows a swimlane diagram of an example process for performing analysis on medical images while preserving private information on clinical-data infrastructure and with reduced redundancy.

FIG. 3 shows a swimlane diagram of an example process 300 for performing analysis on medical images while preserving private information on clinical-data infrastructure and with reduced redundancy.

The medical imager 102 represents any sort of device that generates medical images, including DICOM or similar images. Examples include MIII machines, computed tomography machines, X-Ray machines, and ultrasound machines, which can be used in fields including, but not limited to, radiology, cardiology, oncology, nuclear medicine, radiotherapy, neurology, orthopedics, obstetrics, gynecology, ophthalmology, dentistry, maxillofacial surgery, dermatology, pathology, clinical trials, veterinary medicine, and medical/clinical photography.

The clinical-data client 108 represents a general purpose or specific computing device that provides a user with interface elements to manipulate data, including the uploading of imaging data to a cloud-service provider 112. This can include laptop or desktop computers, workstations, servers, telephone devices, tablet devices, control-panels attached to or incorporated with the medical imager 102, etc.

A gap server 302 represents one or more physical or virtual infrastructure elements that reside on the same clinical-data infrastructure as the medical imager 102 and/or the clinical-data client 108. For example, the gap server may include a physical gateway on the same local network as the imager 102 and the client 108, and some or all of the traffic going in and out of that local network can pass through the gap server 302. In addition, the gap server may include one or more datastores that store private information about patients, operation data for the clinic (e.g., employee scheduling and contact information), or other data. It will be understood that the clinical-data infrastructure may in some cases be confined to a single location, or may be distributed across multiple locations that are geographically separated.

In general, the elements of the clinical-data infrastructure fall under a single administrative scheme, though other arrangements are possible. That is to say, a single administrative team, possibly with different sub-teams, may be responsible for the installation, upkeep, security, and operations of the clinical-data infrastructure. For example, administrators may be responsible for installing software on the client 108 that connects with the imager 102 and transmits, through the gap server 302, to the cloud-service provider 112. Furthermore, the administrative team may also be responsible for setting up and maintaining the gap server 302.

The medical imager generates DICOM data 304. For example, an MRI machine may be used to perform an fMRI on a patient by repeatedly scanning the patient's brain to record brain activity over time. These readings may be recorded in a group of 2D images stored in the DICOM format, along with associated metadata for each image. As will be understood, such a format will produce data that redundantly contains both private and non-private metadata.

The clinical-data client 108 receives the DICOM data 306. For example, the client 108 may be connected by a cable, wireless connection, or data network with the imager 102 to receive the DICOM data from the fMRI study. This DICOM data may be generated in order to send to a cloud-service provider, for example to be subject to complex analysis or used in a cloud-based tool that provides many functions. The DICOM data includes a plurality of images and for each image corresponding metadata, the cloud-service provider being outside of clinical-data infrastructure;

The clinical-data client 108 prepares the DICOM data 308. For example, in response to user input to load the DICOM data from memory, the clinical-data client 108 and/or gap server 302 can prepare, automatically, the DICOM data for transit outside of the clinical-data infrastructure by converting the DICOM data to a NifTI image that is free of private information.

The clinical-data client 108 provides the prepared NifTI image 310. For example, the client 108 and/or gap server 302 can transmit the NifTI image to the gap server 302 to be forwarded to the cloud-service provider 112. In some cases, the client 108 may be configured to only communicate with the gap server. For example, the gap server 302 may be configured as a proxy through which all of the traffic from the client 108 passes, or the gap server may have an agent installed on the client 108's network stack to direct all traffic to the gap server 302. In another example, only a subset of the traffic from the clinical-data client 108 may pass through the gap server 302. For example, the gap server 302 may act as a gateway through which some or all traffic from the client 108 passes before reaching the internet. However, in other examples, the gap server 302 may not be used in the process 300 and the clinical-data client 108 may provide data directly to the service 112. However, this example will be described with a client 108 having instructions to only send data to the cloud-service provider 112 through the gap server 302.

The gap server 302 can encrypt the NifTI image 312. For example, the gap server 302 can encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data. For example, the transmission-image and transmission-metadata may be jointly encrypted into a single cyphertext. In another example, the transmission-image may be encrypted into a first cyphertext and the transmission-metadata may be encrypted into a second cyphertext.

This encryption may be performed with a symmetric key encryption, public key encryption, etc. In one configuration, files are encrypted and compressed by a gap server, and then for communication the encrypted files are again encrypted as part of a TLS or other encrypted format.

This encrypted data may be paired by the gap server 302 with an identifier. This identifier may be a randomly (or pseudorandomly) generated value that uniquely identifies the patient being studied, the study, or another appropriate property of the process 300. The gap server, or another element, may store in a datastore the identifier with data, or pointers to data, that allow information about the study to be pulled up. For example, the identifier may be a patient identifier, and thus queryable in the datastore given the patient identifier in a query. In another example, the study may have a unique identifier, and the datastore may store a table of all studies (or all procedures) that have been performed for a patient. As will be appreciated, other datastore schemes can be used. In another example, private information (or similar such as personal health information) reattached in the random access memory of the gap server 302 as the gap server 302 fetches the private information to connect with the cloud server payload, using the patient file record identifier available in both the clinical-data infrastructure and the cloud-based environment.

The gap server 302 transmits the encrypted NifTI with identifier 314. For example, the gap server 302 can transmit to the cloud-service provider 112 and with the previously discussed identifier, the encrypted transmission-image made from the transmission-image and the encrypted transmission-metadata made from the transmission metadata. As previously explained, the format of such a message may include a single data object to be both the encrypted transmission-image and the encrypted transmission-metadata, or the format may call for two different data objects. The message sending this data can include headers, footers, etc. which can store the unique identifier, or the unique identifier can be stored in the messages payload.

The cloud-service provider 112 receives the NifTI transmission 316, and provider 112 provides analysis 318. For example, the cloud-service provider can receive the transmission and generate a static report based on the data received. In addition or in the alternative, the provider 112 can load the data into a dynamic user interface like a webpage with GUI elements. These GUI elements can provide functionality to generate visual renderings of the data, generate static reports, select one or more tools to manipulate the data, etc.

In order to access the data in plaintext form, the cloud-service provider 112 can decrypt the cyphertext of the message. For example, the provider 112 and the gap server 302 may share symmetrical keys, or the gap server 302 may use the public counterpart to the private key held by the provider 112.

The gap server 302 merges the analysis with private data 320. For example, the gap server 302 can receive a response-message from the cloud-service including the unique identifier; and call up private information related to the study or the patient to incorporate in the analysis. This may take the form of filling in template-fields in a static document, or updating information presented in a dynamic GUI, to name a few of the possible options.

To do this, the gap server can determine that the unique identifier is stored in a private-information datastore previously described, which is indexed with the private information, the private-information datastore also storing additional-private information indexed with other identifiers; and based on the unique identifier, provide the private information and the response-message to a client on the clinical-data infrastructure.

The clinical-data client 108 can receive the analysis and private data 322. For example, the gap server 302 can provide the updated static report to the client 108, or can allow the modified GUI to be rendered on the client 108.

Although a particular configuration of hardware and software is described here, it will be appreciated that other arrangements are possible. For example, the analysis may never be sent to the client 108, but may be sent by the gap server 302 to another element (not shown) on the clinical-data infrastructure. For example, a first clinician may run the study, and then analysis may be sent to a different clinician for their review. In another example, the gap server 302 may not be used. Some or all of the functionality of the gap server 302 may be integrated into another element, including the client 108, or some or all of the functionality of the gap server 302 may not be used. Further, while the data formats of DICOM and NifTI are used to illustrate this example, it will be appreciated that other data formats can be used, including non-standard data formats, archives of image files in formats such as JPEG, tagged image file format (TIFF), or Portable Network Graphic (PNG). In other examples, operations that have been described as being performed by the clinical-data client 108 may be performed by the gap server 302, and vice-versa.

Figure 4:
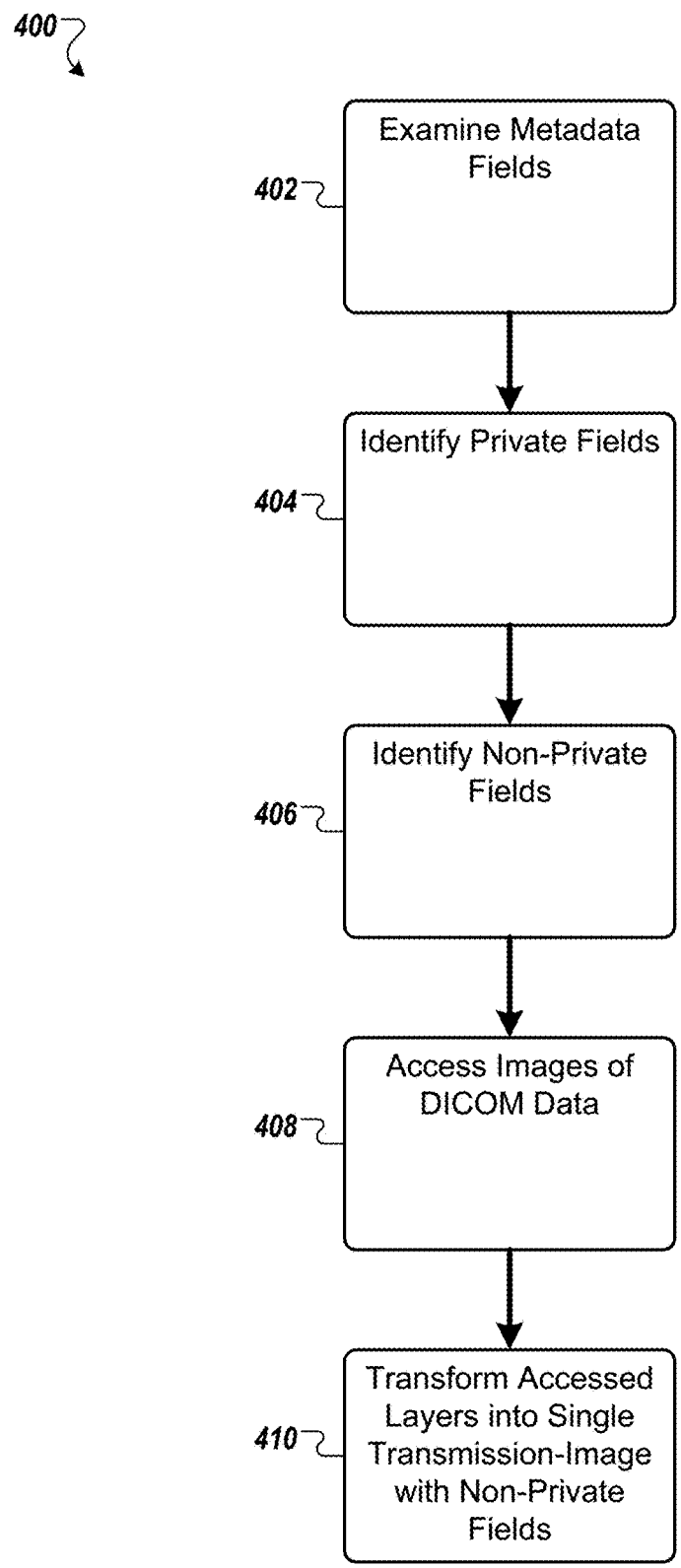
FIG. 4 shows a flowchart of an example process for preparing data for transport.

FIG. 4 shows a flowchart of an example process 400 for preparing data for transport. The process 400 may be used, for example, by the client 108 in preparing 308 the DICOM image, though it may be used by other systems for other purposes.

A plurality of metadata fields may be examined 402. For example, in order to examine a plurality of metadata fields in the metadata in the DICOM data, the client 108 can load into memory the metadata fields of one of the metatdata files of the DICOM image and compare them with private vs. non-private criteria. This critera may include a blacklist or whitelist of fields, text-searching expressions like regular expressions, etc.

Private fields can be identified 404 and non-private fields can be identified 406. For example, the client 108 can identify a first subset of the metadata fields as containing private information and can identify a second subset of the metadata fields as private-information free. For example, the client 108 can initially assign each metadata field to be private, and then any that pass a whitelist test may be marked as non-private.

Layers of the DICOM data are accessed 408. For example, the client 108 can access at least some of the plurality of layers of the DICOM data by loading into memory all layers from a single pass, which will be converted into a single NifTI image.

The accessed layers are transformed into a transmission-image 410. For example, the client 108 may generate, from the loaded layers, a single 3D, voxel based, NifTI image. This process may be repeated for each pass of the DICOM data, such that no image data from the DICOM is lost. However, in other configurations, this may be a lossy process where unneeded or unwanted image data is discarded.

In this way, the client 108 can transform the accessed layers into a single transmission-image, the transmission-image being in a format i) other than DICOM and ii) that stores the second subset of the metadata fields as transmission-metadata in a scheme that is non-redundant for a given transmission-image. One such example used here is NifTI, but it will be understood that other formats may be used.

The client 108 can maintain, with the transmission image, transmission-metadata created from the second subset of the metadata fields. For example, the non-private metadata may be copied to the NifTI image. This maintenance may be configured, such that the transmission-metadata is stored in computer-memory free of redundancy beyond disk-redundancy to which other data stored in the memory is subjected to and the transmission-metadata is free of the private information of the first subset of the metadata fields in the DICOM data. For example, a disk manager may write everything redundantly to disk, the NifTI may be free of the logical redundancy which DICOM specifies.

Figure 5:
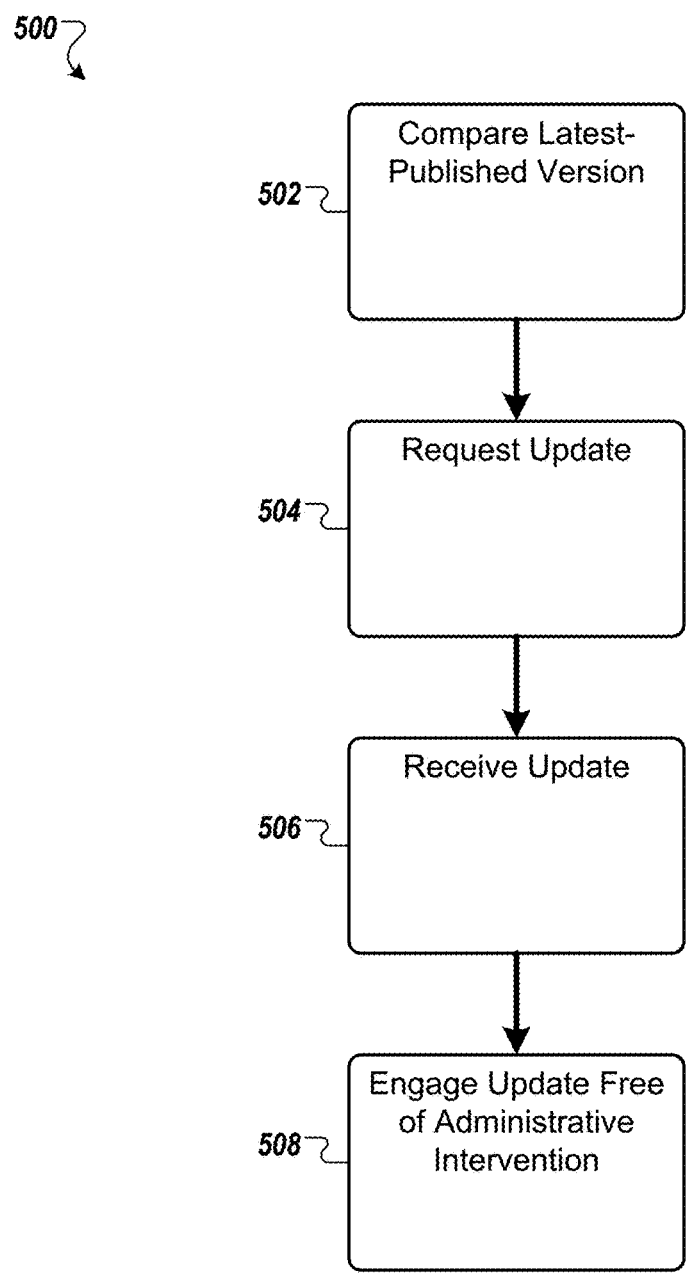
FIG. 5 shows a flowchart of an example process for upgrading software.

FIG. 5 shows a flowchart of an example process 500 for upgrading software. The process 400 may be used, for example, by the client 108 though it may be used by other systems for other purposes.

The process 500 may be performed, e.g., periodically, by the software running on the client 108. For example, a browser (e.g., web browser, file browser) may perform this process 500 on start-up to determine if plug-ins to handle DICOM images are up to date. The process 500 may therefore advantageously keep the client 108 up to date without requiring any specific user input. This may reduce the complexity of client 108 in both use and administration.

A latest-published version is compared 502. For example, the client 108 can compare, before receiving an update message, instructions with a latest-published version hosted by the cloud-service provider to determine if the instructions are out of date. The client 108 can compare this latest-published version with the version of software installed, and if the versions match, the client 108 can determine that the software is up-to-date. However, if the versions do not match, the client 108 can determine that at least some components of the software are out of date.

An update is requested 504. For example, responsive to determining that instructions are out of date, the client 108 can request an update message. The update message may include, for example, information about the client 108, the software as a whole, the software components that are out of date, etc. As will be understood, the software may include a plurality of components that may be updated piecemeal. In another configuration, the entire software package may need to be updated at once.

An update is received 508. For example, the client 108 can receive, from the cloud-service provider, an update message with an update to the instructions of the software. The update may include updates to only some, but not all, of the instructions of the software. In some cases, the update may come from a different network address or from hardware controlled by another party, and the service 112 may or may not be the publisher of the software.

An update is engaged free of administrative intervention 508. For example, the client 108 can engage, engaging, free of intervention by administration of the clinical-data infrastructure, an update routine to the instructions. For example, the client may require no administrative permissions or input to update. In order to provide the user, who may not be an administrator, with uninterrupted working experiences, the client 108 may ask the user if they wish to update now or in the future. In some examples the client 108 can engage the update routes without specific user input and without specific user output. That is, the client 108 may update in the background without affecting the GUI or other interactions of the user.

Figure 6A:
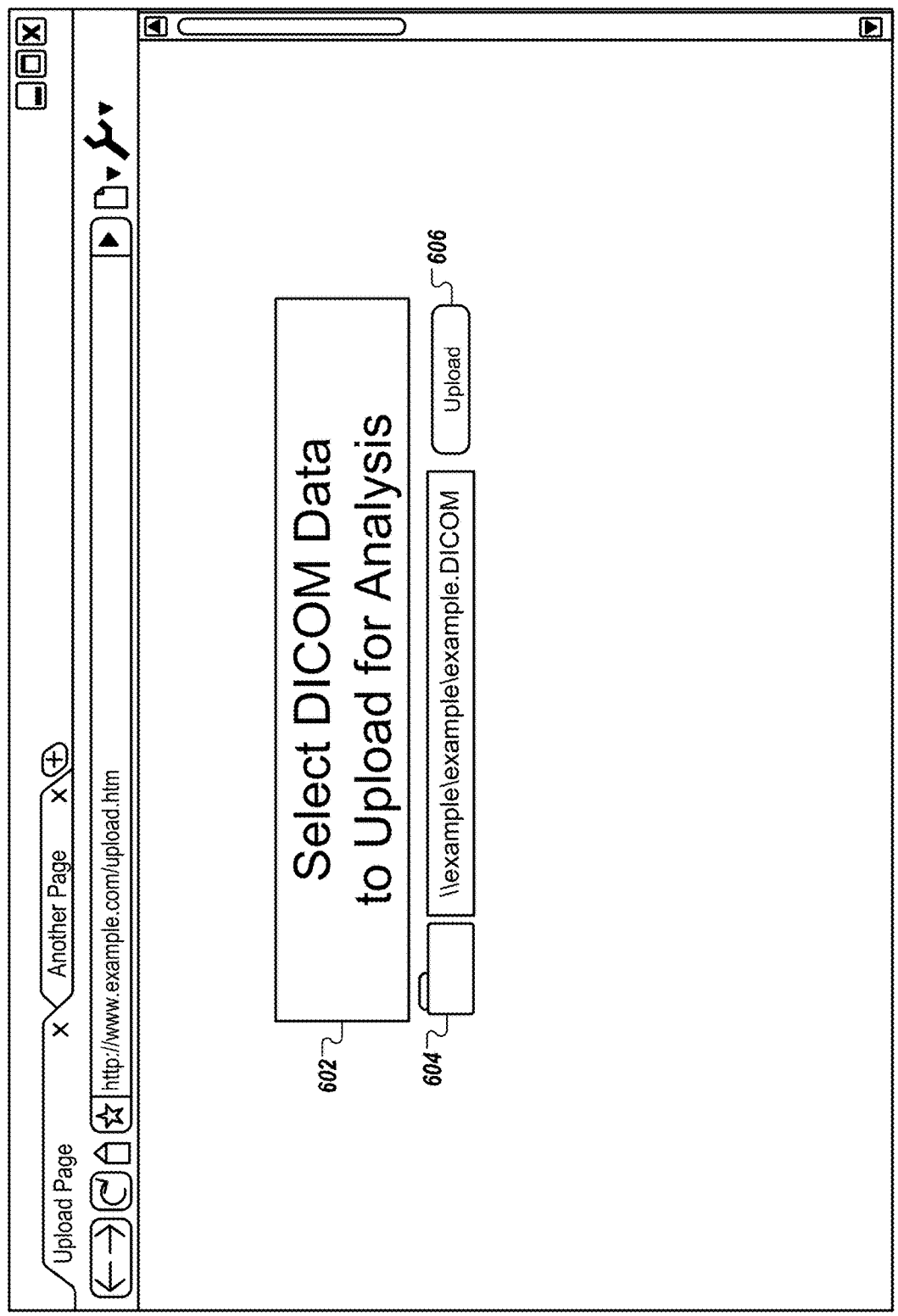
FIGS. 6A and 6B show example GUI.
Figure 6B:
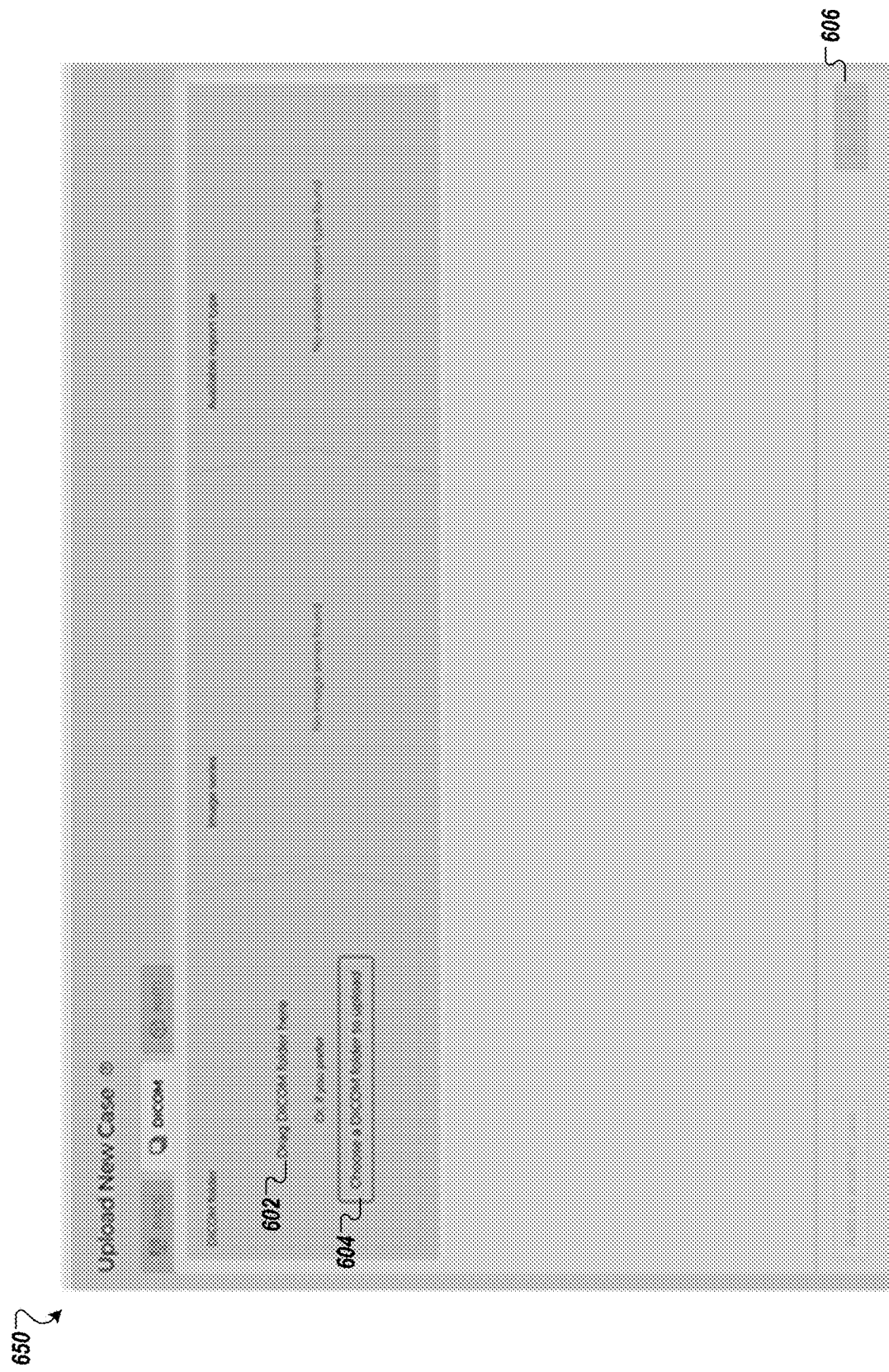

FIGS. 6A and 6B show example GUIs 600 and 650. The GUIs may be presented by the client 108 based on data received from the service 112. As shown here, the GUI is a web browser rendering a webpage served by the service 112. However, other configurations are possible, including stand-alone applications that generate their own interface.

The GUI 600 includes instructions 602 to upload data. These instructions can be rendered in the form of text, images, or other glyphs intended to be understood by the user. Notably, the instructions 602, and indeed the entire GUI 600, may be free of any mention of data conversion and the removal of private information. While these operations are performed in the background, they need not necessarily be presented to the user. This may advantageously reduce the complexity of the GUI 600, increasing its efficiency.

A file-selector 604 can be used to cause the client 108 to receive the DICOM data to be sent to the cloud-service provider 112. The user may then press an upload button 606 to instruct the client 108 to transmit the data of the study to the cloud-service provider 112. By providing these transmission-specific user input, the client 108 can perform the conversion and privacy protection measures described in this document.

Figure 7:
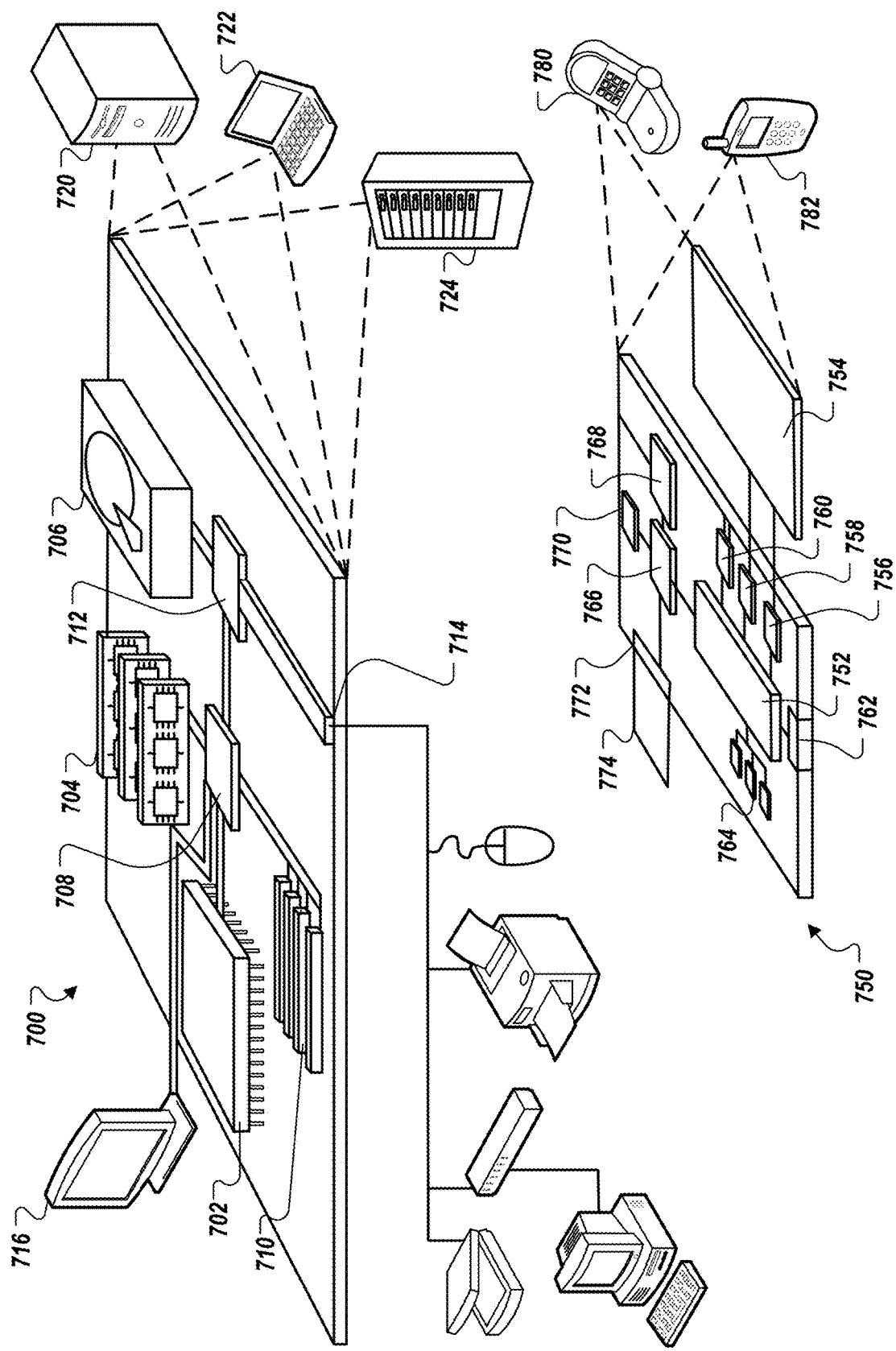
FIG. 7 is a schematic diagram that shows an example of a computing device and a mobile computing device.

FIG. 7 shows an example of a computing device 700 and an example of a mobile computing device that can be used to implement the techniques described here. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 can also be another form of computer-readable medium, such as a magnetic or optical disk.

The storage device 706 is capable of providing mass storage for the computing device 700. In some implementations, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device (not shown), such as a mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage. Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication in some implementations, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provide as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 780. It can also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

What is claimed is:

1. A computer-readable non-transitory storage media for prevention of egress of private information from a clinical data-infrastructure, the computer-readable media storing instructions that, when executed by one or more processors, cause the one or more processors to perform operations comprising:

receiving, at clinical-data infrastructure, Digital Imaging and Communication in Medicine (DICOM) data to be sent to a cloud-service provider, the DICOM data comprising a plurality of images and for each image corresponding metadata, the cloud-service provider being outside of clinical-data infrastructure, the clinical-data infrastructure comprising a clinical-data client and a gap server on a same local network, the clinical-data infrastructure configured to pass traffic, going out of the local network to the cloud service provider, through the gap server;

preparing, automatically, the DICOM data for transit outside of the clinical-data infrastructure, by:
      examining a plurality of metadata fields in the corresponding metadata in the DICOM data;
      identifying a first subset of the metadata fields as containing private information;
      identifying a second subset of the metadata fields as private-information free;
      accessing at least two of the plurality of images of the DICOM data; and
      transforming the accessed images into a single transmission-image, the transmission-image being in a format i) other than DICOM and ii) that stores the second subset of the metadata fields as transmission-metadata in a scheme that is non-redundant for a given transmission-image; and instantiating the gap server configured to:
      encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data, wherein the private information does not leave the clinical-data infrastructure;
      transmit to the cloud-service provider and with a unique identifier, an encrypted transmission-image made from the transmission-image and an encrypted transmission-metadata made from the transmission metadata without transmitting the private information outside the clinical data infrastructure;
      receive, at the gap server, a response-message from the cloud-service including the unique identifier; and
      determine that the unique identifier is stored in a private-information datastore indexed with the private information, the private-information datastore also storing additional-private information indexed with other identifiers; and
      based on the unique identifier, provide the private information and the response-message to a client on the clinical-data infrastructure.

2. The non-transitory storage media of claim 1, wherein the clinical-data infrastructure is maintained under a single administrative scheme and wherein a single administrative team is responsible for the security and operations of the clinical-data infrastructure.

3. The non-transitory storage media of claim 1, wherein the gap server is a physical gateway on a same local network as the clinical-data client.

4. The non-transitory storage media of claim 3, wherein the gap server comprises a datastore that stores the private information and wherein providing the private information and the response-message to the client on the clinical-data infrastructure merging the response message and the private information.

5. The non-transitory storage media of claim 1, wherein private information comprises at least one of patient name, birth date, sex, age and weight.

6. The non-transitory storage media of claim 1, wherein the response message comprises at least one of brain network visualization, surgical planning, anomaly detection in brain activity, and segregation of brain networks.

7. The non-transitory storage media of claim 1, wherein identifying a first subset of metadata fields as containing private information comprises loading into memory the metadata fields and comparing them with private vs. non-private criteria and wherein the private and non-private criteria comprises at least one of a blacklist, a whitelist and text searching expressions.

8. The non-transitory storage media of claim 1, wherein transforming the accessed images into a single transmission-image comprises maintaining, with the transmission image, transmission-metadata created from the second subset of the metadata fields, such that:
the transmission-metadata is stored in computer-memory free of redundancy beyond disk-redundancy to which other data stored in the memory is subjected to; and
the transmission-metadata is free of the private information of the first subset of the metadata fields in the DICOM data.

9. The non-transitory storage media of claim 1, wherein the instructions comprise only sending data to the cloud service through the gap server.

10. A clinical-data client for prevention of egress of private information from a clinical data-infrastructure, the clinical-data client is configured to:
receive, at clinical-data infrastructure, Digital Imaging and Communication in Medicine (DICOM) data to be sent to a cloud-service provider, the DICOM data comprising a plurality of images and for each image corresponding metadata, the cloud-service provider being outside of clinical-data infrastructure, the clinical-data infrastructure comprising a clinical-data client and a gap server on a same local network, the clinical-data infrastructure configured to pass traffic, going out of the local network to the cloud service provider, through the gap server;
prepare, automatically, the DICOM data for transit outside of the clinical-data infrastructure, by:
examining a plurality of metadata fields in the corresponding metadata in the DICOM data;
identifying a first subset of the metadata fields as containing private information;
identifying a second subset of the metadata fields as private-information free;
accessing at least two of the plurality of layers of the DICOM data;
transforming the accessed layers into a single transmission-image, the transmission-image being in a format i) other than DICOM and ii) that stores the second subset of the metadata fields as transmission-metadata in a scheme that is non-redundant for a given transmission-image; and
make available the transmission-image and the transmission metadata to the gap server, the gap server configured to:
encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data, wherein the private information does not leave the clinical-data infrastructure;
transmit to the cloud-service provider and with a unique identifier, an encrypted transmission-image made from the transmission-image and an encrypted transmission-metadata made from the transmission metadata without transmitting the private information outside the clinical-data infrastructure;
receive, at the gap server, a response-message from the cloud-service including the unique identifier; and
determine that the unique identifier is stored in a private-information datastore indexed with the private information, the private-information datastore also storing additional-private information indexed with other identifiers; and
based on the unique identifier, provide the private information and the response-message to a client on the clinical-data infrastructure.

11. The clinical-data client of claim 10, wherein the clinical-data infrastructure is maintained under a single administrative scheme and wherein a single administrative team is responsible for the security and operations of the clinical-data infrastructure.

12. The clinical-data client of claim 10, wherein the gap server is a physical gateway on a same local network as the clinical-data client.

13. The clinical-data client of claim 12, wherein the gap server comprises a datastore that stores the private information and wherein providing the private information and the response-message to the client on the clinical-data infrastructure merging the response message and the private information.

14. The clinical-data client of claim 10, wherein private information comprises at least one of patient name, birth date, sex, age and weight.

15. The clinical-data client of claim 10, wherein the response message comprises at least one of brain network visualization, surgical planning, anomaly detection in brain activity, and segregation of brain networks.

16. The clinical-data client of claim 10, wherein identifying a first subset of metadata fields as containing private information comprises loading into memory the metadata fields and comparing them with private vs. non-private criteria and wherein the private and non-private criteria comprises at least one of a blacklist, a whitelist and text searching expressions.

17. The clinical-data client of claim 10, wherein transforming the accessed layers into a single transmission-image comprises maintaining, with the transmission image, transmission-metadata created from the second subset of the metadata fields, such that:
the transmission-metadata is stored in computer-memory free of redundancy beyond disk-redundancy to which other data stored in the memory is subjected to; and
the transmission-metadata is free of the private information of the first subset of the metadata fields in the DICOM data.

18. The clinical-data client of claim 10, wherein the instructions comprise only sending data to the cloud service through the gap server.

19. A software browser for prevention of egress of private information from a clinical data-infrastructure, the browser being capable of executing native-level executable instructions as well as capable of executing non-native-level executable instructions, at least some of the native-level executable instructions configured to cause the browser, when executed, to:
- receive, at clinical-data infrastructure, Digital Imaging and Communication in Medicine (DICOM) data to be sent to a cloud-service provider, the DICOM data comprising a plurality of images and for each image corresponding metadata, the cloud-service provider being outside of clinical-data infrastructure, the clinical-data infrastructure comprising a clinical-data client and a gap server on a same local network, the clinical-data infrastructure configured to pass traffic, going out of the local network to the cloud service provider, through the gap server;
- prepare, automatically, the DICOM data for transit outside of the clinical-data infrastructure, by:
  - examining a plurality of metadata fields in the corresponding metadata in the DICOM data;
  - identifying a first subset of the metadata fields as containing private information;
  - identifying a second subset of the metadata fields as private-information free;
  - accessing at least two of the plurality of layers of the DICOM data; and
  - transforming the accessed layers into a single transmission-image, the transmission-image being in a format i) other than DICOM and ii) that stores the second subset of the metadata fields as transmission-metadata in a scheme that is non-redundant for a given transmission-image; and
- make available the transmission-image and the transmission metadata to the gap server, the gap server configured to:
  - encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data, wherein the private information does not leave the clinical-data infrastructure;
  - transmit to the cloud-service provider and with a unique identifier, an encrypted transmission-image made from the transmission-image and an encrypted transmission-metadata made from the transmission metadata without transmitting the private information outside the clinical data infrastructure;
  - receive, at the gap server, a response-message from the cloud-service including the unique identifier; and
  - determine that the unique identifier is stored in a private-information datastore indexed with the private information, the private-information datastore also storing additional-private information indexed with other identifiers; and
  - based on the unique identifier, provide the private information and the response-message to a client on the clinical-data infrastructure.

20. A method of preventing egress of private information from a clinical data-infrastructure, the method comprising:
- receiving, at clinical-data infrastructure, Digital Imaging and Communication in Medicine (DICOM) data to be sent to a cloud-service provider, the DICOM data comprising a plurality of images and for each image corresponding metadata, the cloud-service provider being outside of clinical-data infrastructure, the clinical-data infrastructure comprising a clinical-data client and a gap server on a same local network, the clinical-data infrastructure configured to pass traffic, going out of the local network to the cloud service provider, through the gap server;
- preparing, automatically, the DICOM data for transit outside of the clinical-data infrastructure, by:
  - examining a plurality of metadata fields in the corresponding metadata in the DICOM data;
  - identifying a first subset of the metadata fields as containing private information;
  - identifying a second subset of the metadata fields as private-information free;
  - accessing at least two of the plurality of images of the DICOM data; and
  - transforming the accessed images into a single transmission-image, the transmission-image being in a format i) other than DICOM and ii) that stores the second subset of the metadata fields as transmission-metadata in a scheme that is non-redundant for a given transmission-image; and
- instantiate the gap server configured to:
  - encrypt the transmission-image and the transmission-metadata into an encrypted transmission-image and encrypted transmission-metadata, both the encrypted transmission-image and the encrypted transmission-metadata being free of the private information of the first subset of the metadata fields of the DICOM data, wherein the private information does not leave the clinical-data infrastructure;
  - transmit to the cloud-service provider and with a unique identifier, an encrypted transmission-image made from the transmission-image and an encrypted transmission-metadata made from the transmission metadata without transmitting the private information outside the clinical data infrastructure;
  - receive, at the gap server, a response-message from the cloud-service including the unique identifier; and
  - determine that the unique identifier is stored in a private-information datastore indexed with the private information, the private-information datastore also storing additional-private information indexed with other identifiers; and
  - based on the unique identifier, provide the private information and the response-message to a client on the clinical-data infrastructure.

* * * * *